United States Patent [19]

Ragsdale

[11] 4,164,863
[45] Aug. 21, 1979

[54] SYSTEM AND METHOD FOR ANALYZING TONOSIGNALS

[75] Inventor: Charles W. Ragsdale, Garden Grove, Calif.

[73] Assignee: Cavitron Corporation, New York, N.Y.

[21] Appl. No.: 839,584

[22] Filed: Oct. 5, 1977

[51] Int. Cl.² ............................................. A61B 3/16
[52] U.S. Cl. ................................................. 128/652
[58] Field of Search ...................... 73/80, 81; 128/2 T

[56] References Cited

U.S. PATENT DOCUMENTS

| | | | |
|---|---|---|---|
| 3,406,565 | 10/1968 | Murr | 73/80 |
| 3,992,926 | 11/1976 | Berryhill | 73/80 |

Primary Examiner—Anthony V. Ciarlante
Attorney, Agent, or Firm—Flehr, Hohbach, Test, Albritton & Herbert

[57] ABSTRACT

A system and method analyzes tonosignals and other electrical signals representative of force-displacement information from applanating probes such as those initially to determine the presence of an acceptable waveform or tonosignal. Once an acceptable waveform is found, that waveform is analyzed further to locate the point of applanation. The level of the waveform at that point may be converted to a digital signal and displayed to indicate the pressure within the eye or other objects to which the probe is applied.

24 Claims, 8 Drawing Figures

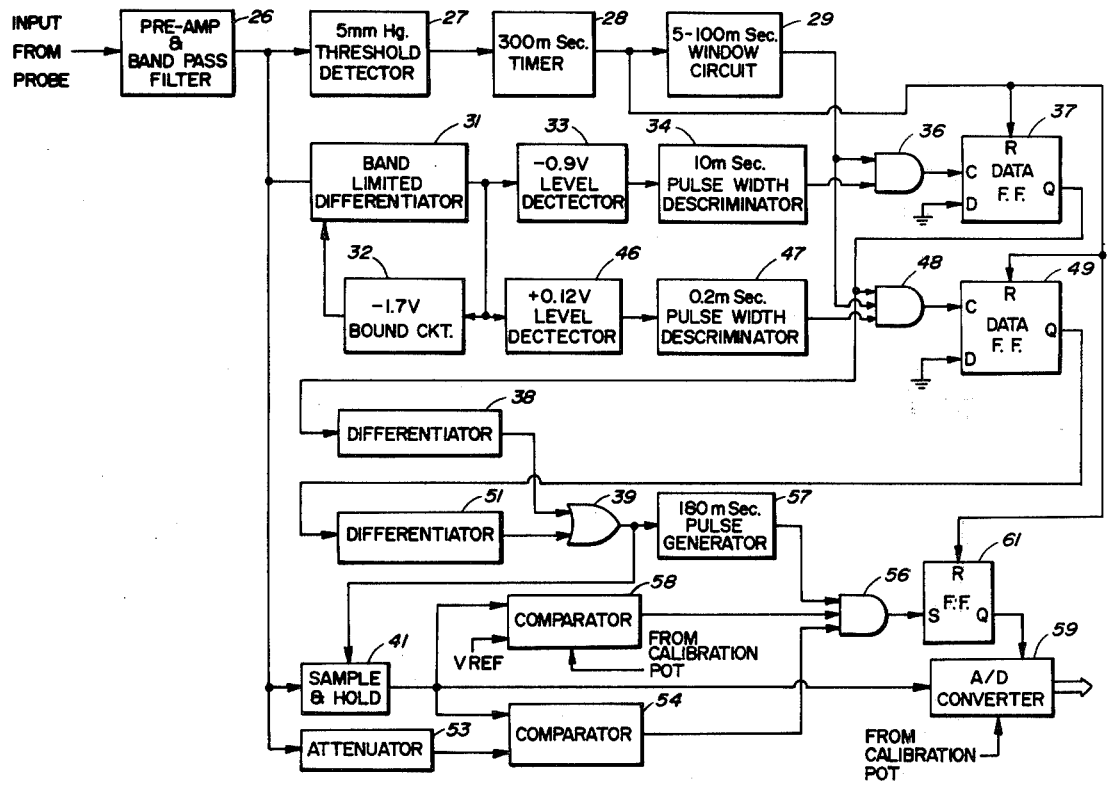

SYSTEM AND METHOD FOR ANALYZING TONOSIGNALS

BACKGROUND OF THE INVENTION

This invention pertains generally to the measurement of the internal pressure of an object such as the eye and more particularly to a system and method for analyzing signals produced by an applanating probe applied externally to the object.

Heretofore, applanating tonometers have been developed for use in determining intra-occular pressure without penetration of the eye. Such devices generally include a probe which is pressed against the cornea to flatten a portion thereof, and the force required to do the flattening is monitored to determine the pressure within the eye. The electrical waveforms or tonosignals produced by these probes are frequently transcribed and as transcribed are known as tonograms. An ideal tonogram is illustrated in FIG. 1.

From this figure it will be noted that the force on the probe increases initially, as indicated at 11, as the probe is brought into contact with the eye. While the cornea is being applanated a knee or breakpoint 13 occurs, and the force then decreases as indicated at 14. Thereafter, as the probe continues to press against the eye, the force increases to an overpressure as indicated at 16, with a notch or valley 17 between decrease 14 and increase 16. At the valley 17 a force balance exists at the surface of the eye, and the level of the waveform corresponds to the pressure which exists in the undisturbed eye before the tonometer is applied.

In practice, many tonosignals are encountered which do not have the ideal waveform shown in FIG. 1. Examples of such tonosignals are illustrated in FIGS. 2A–2F. In FIG. 2A, the waveform has a definite breakpoint 13, but no notch or valley 17. In FIG. 2B no overpressure 16 occurs, and this may or may not represent a good waveform, since the absence of overpressure can be due to premature pulling of the probe away from the eye. In FIG. 2C, the effect of hand tremor and/or motion of the probe at the surface of the eye is illustrated. While there are several breakpoints 18 in this waveform, only two (the third and fourth) exist for a sufficient time. Of these two, only one (the third one) is followed by an overpressure and is, therefore, likely to be acceptable. In FIG. 2D, the probe has been bounced at the surface of the eye, resulting in an unusable first waveform 19 and a second waveform 21 which is suspect. In FIG. 2E, the breakpoint 22 is only slight, indicating tight tonotips, improper probe angle or other factors. In FIG. 2F, no sufficient breakpoint exists, and this waveform should also be discarded.

In the past, tonosignals have been analyzed primarily by recording the waveforms on a graphic recorder to produce the tonograms for visual interpretation. This technique has a number of disadvantages, the most significant of which is that the interpretation can only be made by specially trained personnel at some time after the readings have been made and recorded.

There has also been at least one attempt to interpret tonometer signals electronically. U.S. Pat. No. 3,992,926 discloses a technique utilizing double differentiation to locate a point on the waveform to be read. While this approach may eliminate the need for a skilled operator, it is subject to other problems such as erroneous interpretation of some waveforms.

SUMMARY AND OBJECTS OF THE INVENTION

The invention provides a reliable system and method for analyzing an electrical signal and particularly a tonosignal which indicates the pressure within an eye such as displacement information signal from an applanating probe applied to the eye. The signal is analyzed initially to determine the presence of an acceptable waveform. If an acceptable waveform is found, it is analyzed further to locate a notch or valley which, for a tonosignal, indicates the pressure within the eye. The level of the waveform substantially at that point is preferably converted to a digital signal and digitally displayed.

It is in general an object of the invention to provide a new and improved system and method for analyzing tonosignals and other electrical signals representative of force-displacement information from applanating probes.

Another object of the invention is to provide a system and method of the above character in which the signals are analyzed initially to determine the presence of an acceptable waveform and, once identified, the waveform is anlayzed further to determine the point at which the level corresponds to the pressure within the eye.

Additional objects and features of the invention will be apparent from the following description in which the preferred embodiments are set forth in detail in conjunction with the accompanying drawings.

DESCRIPTION OF THE PREFERRED EMBODIMENTS

In the method of the invention, the waveform is monitored initially for a predetermined threshold level, e.g. 1/10 of full scale or 5 mm Hg. This permits the rejection of spurious signals which may occur as the probe is moved into position next to the eye and provides discrimination against low amplitude noise signals. The time between successive threshold crossings is monitored, and the waveform is rejected if a positive going crossing occurs within 300 milliseconds of the negative going (or ending) threshold crossing of the previous waveform. Waveforms occurring at a faster rate may be produced by bouncing the probe on the eye or withdrawing it prematurely, and such waveforms are not reliable.

Figure 1:
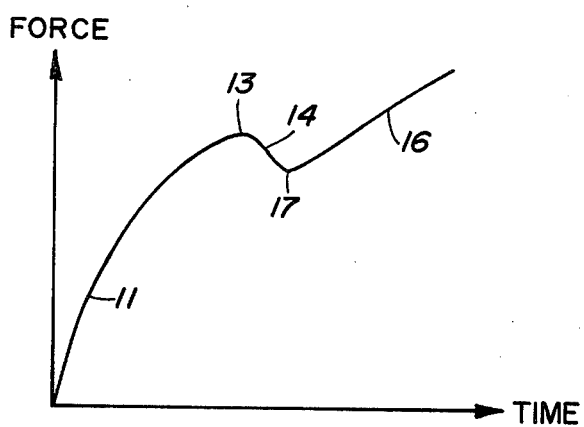
FIG. 1 is a graphical representation of an ideal tonosignal.
Figure 2A:
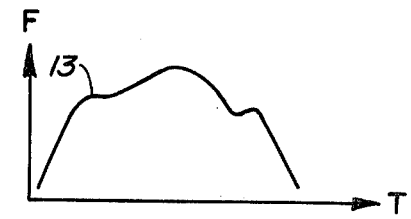
FIGS. 2SA–2F are graphical representations of other tonosignals.
Figure 2B:
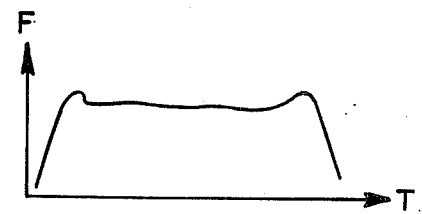
Figure 2C:
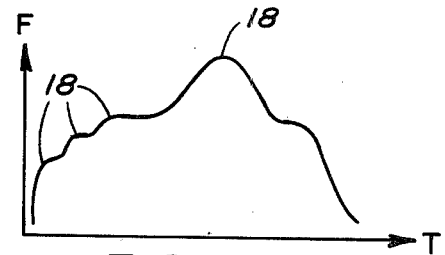
Figure 2D:
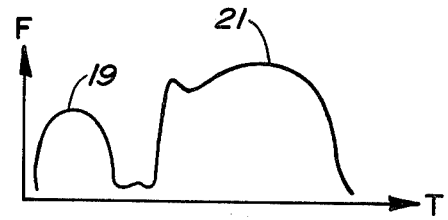
Figure 2E:
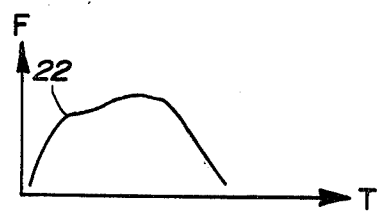
Figure 2F:
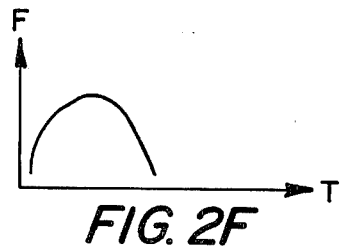

Once the desired threshold crossing is detected, the slope of the waveform is monitored for a change from one positive value (e.g. greater than 9.0 volts/sec where the calibration value is typically 1.5 v per 25 mm Hg) in region 11 as shown in FIG. 1 to a lesser positive value (e.g. .9 volts/sec or less) in region 13 of the ideal waveform. If the change occurs and the reduced (or an even lesser) slope is maintained for a predetermined period (e.g. 10 msec) within an interval commencing 5 msec. after the threshold crossing and ending 100 msec after the crossing, the waveform is considered to be acceptable and a signal corresponding to the level of the waveform is stored. This signal provides a good initial estimate of the pressure within the eye.

The lower limit of the 5-100 msec. window serves to reject waveforms with rise times which are too fast. In such waveforms, the breakpoints may be obliterated, and the waveforms may have peaks which greatly exceed the actual pressure. In addition, the lower limit also serves to limit the rate at which the probe can be applied to the eye, thereby requiring some degree of softness of touch in the application of the probe. The upper limit discriminates against touches of the probe which are so light that they could produce undulations which might be intrepreted as breakpoints.

Once an acceptable waveform has been identified and the initial pressure signal has been stored, the waveform is then analyzed further in order to obtain a pressure reading closer to the notch or valley 17, of the waveform. Toward this end, the slope is checked for a minimum negative value (e.g. −1.2 volts/sec. or more) as found in region 14 of the ideal tonogram. If such a slope is found and maintained for a given time (e.g. 0.2 msec) the slope is then checked for a change to a more positive value, as at the valley 17 of the ideal waveform. If a change to the more positive slope occurs within the 5-100 msec. window, the notch or valley has been located, and a signal corresponding to the level of the waveform at that point is stored in place of the previously stored signal.

Before one of these stored pressure signals is accepted or utilized, the waveform is checked for overpressure, that is a predetermined increase (e.g. 10%) in level from the stored value within a given time (e.g. 180 msec. from the time of the last value storage). In order to discriminate against low level signals which may resemble tonosignals, the level of the stored signal is checked to make certain that the pressure is above a predetermined level (e.g. 10 mm Hg). If these last two conditions are met, the signal then stored is converted to a digital signal and made available to an output device or otherwise utilized to indicate the pressure within the eye.

Figure 3:
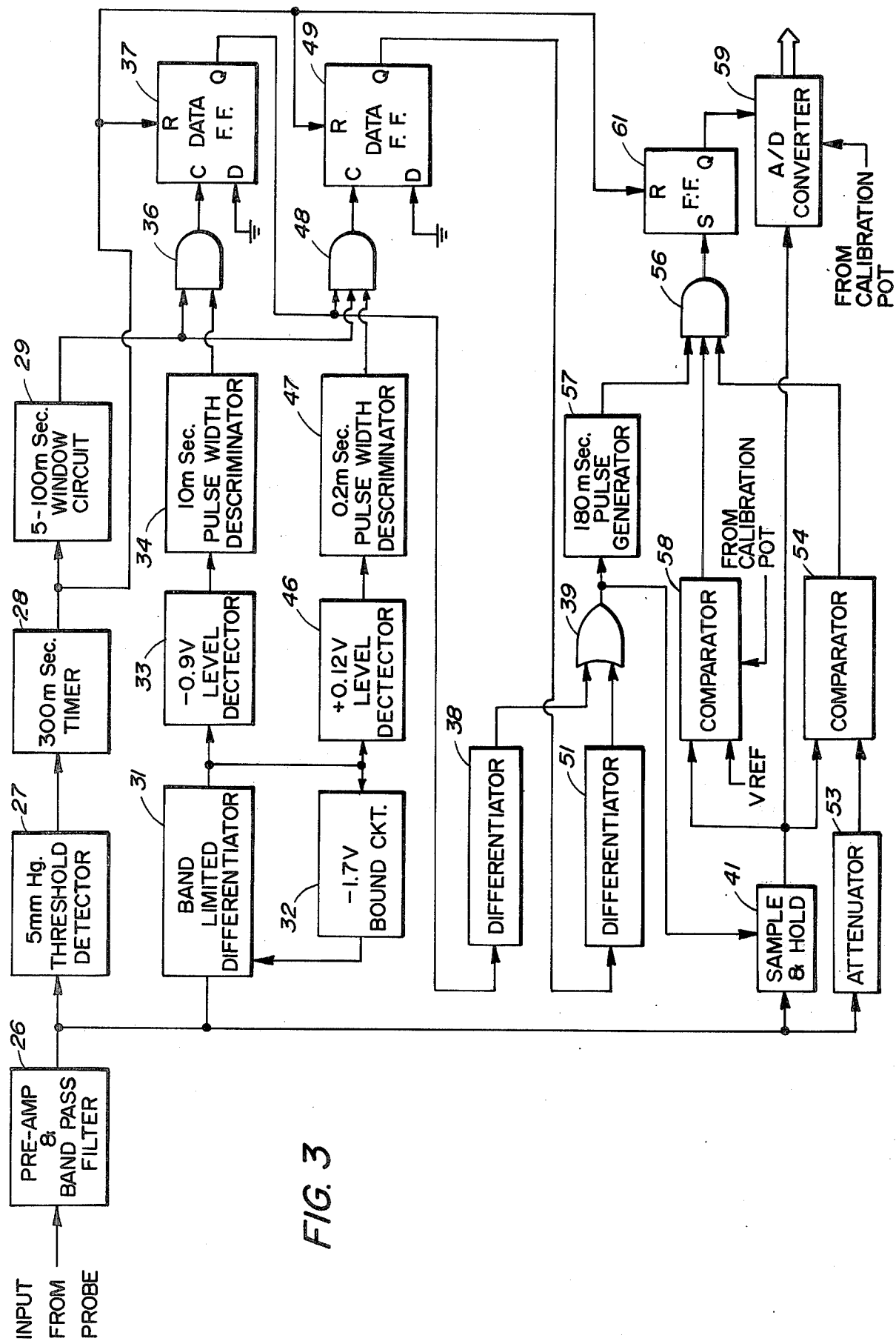
FIG. 3 is a block diagram of a system incorporating the invention for analyzing tonosignals.

In the preferred embodiment, the foregoing method is carried out by the system illustrated in FIG. 3. This system includes a preamplifier and band pass filter 26 to which the input signal from the probe, that is, the tonosignal is applied. Means is provided for monitoring the level of the input signal to determine when it reaches a threshold level corresponding to a certain minimum pressure (e.g. 5 mm Hg). This means comprises a threshold voltage level detector 27 connected to the output of the preampifier and band pass filter.

The output of threshold detector 27 is connected to the input of a 300 msec. timer 28. This timer delivers an output signal which rises upon firing of the threshold detector and falls 300 msec. later. The output of the 300 msec. timer is connected to the input of a 5-100 msec. window circuit 29, which may be in the form of an monostable multivibrator. This window circuit delivers an output signal which rises 5 msec. after the threshold detector fires and falls 95 msec. later, thereby defining a window of 95 msec. duration.

Means is provided for monitoring the slope of the tonosignal. This means includes a band-limited differentiator 31 which, in the preferred embodiment, has a roll-off frequency of 160 Hz. A bound circuit 32 is connected to the differentiator to prevent saturation by signals which rise too rapidly. In the embodiment illustrated, the bound circuit 32 sets a bound of −1.7 volts, which corresponds to a maximum slope of 17 volts/second in region 11 of the tonosignal.

The output of differentiator 31 is connected to the input of a level detector 33 which has a threshold voltage corresponding to the desired maximum positive slope in region 13 of the tonosignal. The output of level detector 33 is connected to the input of a 10 msec. pulse width discriminator 34. The output of the pulse width discriminator is connected as one input of AND gate 36. This gate receives a second input from the output of window circuit 29. The output of AND gate 36 is connected to the input of a flip-flop 37, and this flip-flop receives a RESET signal from timer 28. The output of flip-flop 37 is connected to the input of a differentiator 38, and the output of this differentiator is connected as one input of an OR gate 39. The output of this gate is connected to the control input of a sample and hold circuit 41, to which the signal from preamplifier and filter 26 is also applied.

The output of differentiator 31 is also connected to the input of a level detector 46 which has a threshold voltage corresponding to the minimum negative slope of the tonosignal in region 14. The output of this level detector is connected to the input of a 0.2 msec. pulse width discriminator 47, and the output of this pulse width discriminator is connected to one input of AND gate 48. This gate receives a second input from window circuit 29 and a third input from flip-flop 37. The output of AND gate 48 is connected to the input of a flip-flop 49 which also receives a RESET signal from timer 28. The output of flip-flop 49 is connected to the input of a differentiator 51, and the output of this differentiator is connected to a second input of OR gate 39.

Means is provided for determining when the level of the input signal rises a predetermined amount (e.g. 10%) above the level of the signal stored in the sample and hold circuit. This means includes an attenuator 53 connected to the output of preamplifier and filter 26. The outputs of sample and hold circuit 41 and attenuator 53 are connected to the inputs of a voltage comparator 54, and the output of this comparator is connected to one input of AND gate 56. Means is also provided for determining whether the increase in signal level ocurs within a predetermined time, e.g. 180 msec. This means includes a 180 msec. pulse generator 57 connected between the output of OR gate 39 and a second input of AND gate 56. This gate also receives a third input from a comparator 58 which receives inputs from sample and hold circuit 41, from a calibration potentiometer and from a reference source $V_{Ref}$. This comparator provides discrimination against low level signals having waveforms similar to tonosignals.

Means is included for providing an output signal corresponding to the signal stored in sample and hold circuit 41. This means comprises an analog-to-digital converter 59 connected to the output of the sample and hold circuit. The output of AND gate 56 is connected to the input of a flip-flop 61, and the output of this flip-flop is connected to the control input of the A/D converter. Flip-flop 61 receives a RESET signal from timer 28.

Operation and use of the system of FIG. 3 are as follows. If the amplitude of the signal from preamplifier and filter 26 reaches the threshold level set by threshold detector 27, the output of the threshold detector changes state. This transition triggers timer 28 unless the timer is already in its triggered state, in which case the transition has no effect. Since the timer does not respond to threshold crossings which occur more frequently than the period of the timer (e.g. 300 msec.), tonosignals which occur less than 300 msec. after the preceeding tonosignal are rejected. The rise in the output of timer 28 triggers circuit 29 which then delivers an output signal which rises 5 msec. after triggering and falls 95 msec. thereafter.

The slope of the input signal is monitored by differentiator 31 which produces an output signal corresponding in level to the magnitude of the slope. As long as the slope exceeds +17 volts/second, bound circuit 32 holds the output of the differentiator at −1.7 volts. When the slope drops below +17 volts/second, the bound is released. When the slope becomes less than +9 volts/second, level detector 33 changes its output state. If the reduced slope continues for at least 10 msec., pulse width discriminator 34 delivers a positive output signal to AND gate 36. If this output signal is delivered within the 5–100 msec. window interval defined by circuit 29, flip-flop 37 is triggered. As the output of flip-flop 37 changes state, (that is, 10 msec after the slope drops below +9 volts/second) differentiator 38 delivers a relatively narrow pulse to sample and hold circuit 41 via OR gate 39. This causes the level of the input signal from pre-amp 26 at that time to be stored in the sample and hold circuit 41. Since the level is sampled only 10 msec after the slope drops below 9 volts/second the level of the signal as sampled is substantially the same as that at the region 13. As discussed above, this signal provides a good initial estimate of the pressure within the eye, and the storage of this signal indicates that an acceptable waveform has been identified.

If the slope of the input signal becomes more negative than −1.2 volts/second, level detector 46 changes its output state, and if this slope is maintained for 0.2 msec., pulse width discriminator 47 delivers an output signal to AND gate 48 when the slope becomes more positive than −1.2 volts/second. Upon conjoint receipt of this signal and the 5–100 msec. window signal and the output from the flip-flop 37, AND gate 48 delivers a trigger signal to flip-flop 49. As the output of flip-flop 49 changes state, differentiator 51 delivers a pulse to sample and hold circuit 41 via OR gate 39, and the previously stored signal is replaced with a signal corresponding to the level of the input signal at the present time. Since the level of the new signal is sampled essentially when the slope becomes more positive than −1.2 volts/second the level of this new signal as sampled is substantially the same as that at the valley 17. This new signal, then, very accurately represents the pressure within the eye.

Once a signal is stored in sample and hold circuit 41, comparator 54 compares the attenuated signal from attenuator 53 with the stored signal and delivers an output signal to AND gate 56 if the level of the attenuated input signal reaches the level of the stored signal. The delivery of a pulse from OR gate 39 also triggers pulse generator 57 which then delivers a 180 msec positive pulse to AND gate 56. If the signal stored in the sample and hold circuit exceeds the level set by the $V_{Ref}$ and calibration potentiometer, comparator 58 delivers a third input signal to AND gate 56. Upon conjoint receipt of these three signals, AND gate 56 triggers flip-flop 61, and A/D converter 59 then converts the signal then stored in sample and hold circuit 41 to a digital signal. This signal can be displayed or utilized otherwise as desired to indicate the pressure within the eye.

It is apparent from the foregoing that a new and improved system and method for analyzing electrical signals from tonometers and other applanating probes have been provided. While only the presently preferred embodiments have been described in detail, as will be apparent to those familiar with the art, certain changes and modifications can be made without departing from the scope of the invention as defined by the following claims.

I claim:

1. In a method of analyzing an electrical signal representative of force-displacement information from an applanating probe, the steps of: monitoring the level of said signal and the rate of change of said level to detect occurrence of a waveform of predetermined character at a predetermined time, further monitoring the slope of said waveform to detect the occurrence of a predetermined change in said slope after detection of the occurrence of said waveform of predetermined character, and providing an output signal corresponding substantially to the level of said signal at the time of said change in slope.

2. The method of claim 1 further including the steps of monitoring the level of said signal following detection of said change in slope and utilizing said output signal only in the event that said level changes by a predetermined amount after said change in slope is detected.

3. The method of claim 1 wherein the step of monitoring said signal to detect said occurrence of a waveform of predetermined character comprises ascertaining that said electrical signal exceeds a threshold amplitude value, that said signal's waveform exhibits a slope exceeding a predetermined positive value, and that said signal occurs more than a predetermined time period after any previous signal exceeding said threshold and slope values.

4. The method of claim 3 wherein said predetermined change in said slope is from a slope exceeding said predetermined positive value to a slope of less than said predetermined positive value.

5. The method of claim 1 including the steps of still thereafter monitoring said slope of said waveform to detect a reversal in the polarity of said slope and a predetermined change in the value of the reversed polarity slope, and providing a second output signal corresponding substantially to the level of said signal at the time of said change in said reversal polarity slope.

6. In a system for analyzing an electrical signal representative of force-displacement information from an applanating probe: means for monitoring the level of said signal and the rate of change of said level to detect the occurrence of a waveform of predetermined character at a predetermined time, means for further monitoring the slope of said waveform to detect the occurrence of a predetermined change in said slope after detection of the occurrence of said waveform of predetermined character, and means for providing an output signal corresponding substantially to the level of said signal at the time of said change in slope.

7. The system of claim 6 further including means for monitoring the level of said signal following detection of said change in slope and utilizing said output signal only in the event that said level changes by a predetermined amount after said change in slope is detected.

8. The system of claim 6 wherein said means for monitoring said signal to detect said occurrence of a waveform of predetermined character comprises means for ascertaining that said electrical signal exceed a threshold amplitude value, that said signal's waveform exhibits a slope exceeding a predetermined positive value, and that said signal occurs more than a predetermined time period after any previous signal exceeding said threshold and slope values.

9. The system of claim 8 wherein said predetermined change in said slope is from a slope exceeding said predetermined positive value to a slope of less than said predetermined positive value.

10. The system of claim 6 together with means for still thereafter monitoring the slope of said waveform to detect a reversal in the polarity of said slope and a predetermined change in value of the reversed polarity slope, and means for providing a second output signal corresponding substantially to the level of said signal at said time of the change in said reversed polarity slope.

11. In a method of analyzing an electrical probe signal representative of force-displacement information from an applanating probe, the steps of: monitoring the level of said probe signal and the rate of change of said level to detect the occurrence of a waveform of predetermined character within a predetermined period of time, storing a first output signal corresponding to the level of the probe signal upon detection of said waveform of predetermined character, monitoring the slope of said waveform to detect the occurrence of a predetermined change in said slope, storing a second output signal corresponding substantially to the level of said waveform upon detection of said change in slope, and providing a utilization signal corresponding to the last stored of said first and second output signals.

12. The method of claim 11 including the steps of further monitoring the level of said probe signal and for providing said utilization signal only in the event that the level of said probe signal changes by a predetermined amount from the level corresponding to said last stored output signal.

13. The method of claim 11 further including the steps of converting said utilization signal to a digital signal representative of the pressure within an object to which the probe is applied.

14. In a system for analyzing an electrical probe signal representative of force-displacement information from an applanating probe: means for monitoring the level of said probe signal and the rate of change of said level to detect the occurrence of a waveform of predetermined character within a predetermined period of time, means for storing a first output signal corresponding to the level of the probe signal upon detection of said waveform of predetermined character, means for monitoring the slope of said waveform to detect the occurrence of a predetermined change in said slope, means for storing a second output signal corresponding substantially to the level of said waveform upon detection of said change in slope, and means for providing a utilization signal corresponding to the last stored of said first and second output signals.

15. The system of claim 14 together with means for further monitoring the level of said probe signal and for providing said signal only in the event that the level of said probe signal changes by a predetermined amount from the level corresponding to said last stored output signal.

16. The system of claim 14 further including means for converting said utilization signal to a digital signal representative of the pressure within an object to which the probe is applied.

17. In a method of analyzing an electrical probe signal representative of force-displacement information from an applanating probe, the steps of:
   A. Monitoring said probe signal to determine whether the following conditions are met:
      1. Said probe signal reaches a predetermined threshold level at least a predetermined minimum time after any previous reaching of said level,
      2. The level of said probe signal changes at a positive rate which decreases within a predetermined time window which commences a predetermined time after said threshold level is reached,
      3. The decreased rate of change continues for a predetermined period of time within said time window; and
   B. In the event that all of said conditions are met, providing an output signal corresponding to the level of said probe signal at the time said conditions are met.

18. The method of claim 17 further including the steps of:
   C. Storing said output signal;
   D. Further monitoring said probe signal to determine whether the following additional conditions are also met:
      1. The level of said probe signal changes at a predetermined negative rate for a predetermined time after said first named conditions are met, and
      2. Thereafter, but still within said time window the level changes to a less negative rate;
   E. In the event that said additional conditions are met, storing a second output signal corresponding to the level of said probe signal at the time said additional conditions are met; and
   F. Delivering an utilization signal corresponding to the last stored of said output signals.

19. The method of claim 18 including the steps of further monitoring the level of said probe signal after storage of said last stored output signal and delivering said utilization signal only in the event that the level of said probe signal increases by a predetermined amount from the level corresponding to said last stored output signal and within a predetermined time from storing said last output signal.

20. The method of claim 18 wherein said utilization signal is a digital signal representative of the pressure within an object to which the probe is applied.

21. In a system for analyzing an electrical probe signal representative of force-displacement information from an applanating probe:
   A. Means for monitoring said probe signal to determine whether the following conditions are satisfied:
      1. Said probe signal reaches a predetermined threshold level at least a predetermined minimum time after any previous reaching of said level,
      2. The level of the probe signal changes at a positive rate which decreases within a predetermined time window which commences a predetermined time after said threshold level is reached,
      3. The decreased rate of change continues for a predetermined period of time within said time window; and B. Means active upon satisfaction of all of said conditions for providing an output signal corresponding to the level of said probe signal at the time said conditions are satisfied.

22. The system of claim 21 further including:
C. Means for storing said output signal;
D. Means for further monitoring said probe signal to determine whether the following additional conditions are also satisfied:
 1. The level of said probe signal changes at a predetermined negative rate for a predetermined time after said first named conditions are met, and
 2. Thereafter, but still within said time window the level changes to a less negative rate;
E. Means active upon satisfaction of said additional conditions for storing a second output signal corresponding to the level of said probe signal at the time said additional conditions are met; and
F. Means for delivering an utilization signal corresponding to the last stored of said output signals.

23. The system of claim 22, together with means for further monitoring the level of said probe signal after storage of said last stored output signal and delivering said utilization signal only in the event that the level of said probe signal increases by a predetermined amount from the level corresponding to said last stored output signal and within a predetermined time from storing said last stored output signal.

24. The system of claim 22 wherein said utilization signal is a digital signal representative of the pressure within an object to which the probe is applied.

* * * * *